(12) United States Patent
Jiang

(10) Patent No.: US 9,039,968 B2
(45) Date of Patent: May 26, 2015

(54) SMART HOME SYSTEM AND OPERATION METHOD THEREOF

(76) Inventor: Hong Jiang, Zhuhai (CN)

( * ) Notice: Subject to any disclaimer, the term of this patent is extended or adjusted under 35 U.S.C. 154(b) by 0 days.

(21) Appl. No.: 14/008,389

(22) PCT Filed: Mar. 22, 2012

(86) PCT No.: PCT/CN2012/072805
§ 371 (c)(1),
(2), (4) Date: Sep. 27, 2013

(87) PCT Pub. No.: WO2012/130082
PCT Pub. Date: Oct. 4, 2012

(65) Prior Publication Data
US 2014/0023556 A1    Jan. 23, 2014

(30) Foreign Application Priority Data

Mar. 29, 2011    (CN) .......................... 2011 1 0077696

(51) Int. Cl.
| | | |
|---|---|---|
| A61L 9/00 | (2006.01) |
| B01D 47/02 | (2006.01) |
| B01L 1/04 | (2006.01) |
| B67D 1/08 | (2006.01) |
| A61L 2/24 | (2006.01) |
| C01B 13/10 | (2006.01) |
| G05B 19/43 | (2006.01) |

(52) U.S. Cl.
CPC . A61L 2/24 (2013.01); C01B 13/10 (2013.01); G05B 19/43 (2013.01)

(58) Field of Classification Search
CPC ............. A61L 9/01; A61L 2/00; A61L 2/183; A61L 2/202; A47K 17/00; B01F 3/04099; C02F 1/78
USPC ........ 422/1, 28, 32–33, 62, 110, 119, 186.07, 422/292, 305; 261/76, DIG. 17, DIG. 42, 261/133; 454/187; 366/101; 204/176; 210/76; 73/23.41; 222/148
See application file for complete search history.

(56) References Cited

U.S. PATENT DOCUMENTS 5,106,589 A  *  4/1992   Conrad .................... 422/186.15
2005/0150967 A1     7/2005   Chapman, Jr. et al.

FOREIGN PATENT DOCUMENTS

| CN | 101266488 | 9/2008 |
| CN | 101748773 | 6/2010 |
| CN | 101957618 | 1/2011 |
| CN | 102122166 | 7/2011 |
| JP | 10307107 | 11/1998 |

* cited by examiner

*Primary Examiner* — Monzer R Chorbaji
(74) *Attorney, Agent, or Firm* — Cozen O'Connor

(57) ABSTRACT

A smart home system having a controller which controls an ozone generator, gas supply outlets connected to gas supply outlets of the ozone generator via a pipe, and solenoid valves which control opening and closing of the gas supply outlets. The controller is connected with each of the solenoid valves and controls opening and closing of each of the solenoid valves. An operation method for the system discloses driving the ozone generator by the controller to generate ozone, controlling opening of the solenoid valves by the central processor when the central processor receives an external signal for opening the solenoid valves, reducing opening level of the solenoid valves when a gas flow sensor detects that the ozone flow rate passing through the gas inlet is greater than the flow rate threshold, and controlling closing of the solenoid valves by the central processor when the central processor receives a signal for closing the solenoid valves.

15 Claims, 4 Drawing Sheets

SMART HOME SYSTEM AND OPERATION METHOD THEREOF

CROSS-REFERENCE TO RELATED APPLICATIONS

This application claims priority from international application No. PCT/CN2012/072805 filed on Mar. 22, 2012, which claims priority from Chinese Patent Application Number 201110077696.4, filed on Mar. 29, 2011. These applications are incorporated herein by reference.

FIELD OF THE INVENTION

The invention relates to the field of smart control. More particularly, the invention relates to a smart home system and its operation method.

TECHNICAL BACKGROUND

As living standard rises, people are looking for healthy and safe home systems to improve their quality of life. The general idea for designing existing smart home systems mainly focus on people's health by providing ozone water for disinfection and sterilization and supplies negative ions-containing fresh air.

For instance, Chinese Invention Patent Application Publication No. CN101303093A discloses a faucet which supplies ozone. The faucet has a water outlet pipe. One end of the water outlet tube is connected with a gas outlet of an ozone generator. The faucet is provided with a mixer where the water outlet pipe and the gas outlet pipe meet. Ozone from the ozone generator is mixed with tap water to form ozone water. Therefore, when the user turns on the tap water, the water dissolves ozone and the ozone water can be used for disinfecting, cleaning and washing.

Technical Problems

However, the above faucet requires one ozone generator for each faucet. For homes which have multiple faucets, many ozone generators would be needed. This could be costly. In addition, each faucet requires one ozone generator to be installed nearby. The ozone generator needs power, and therefore a power plug is needed near the faucet. If water splashes into the power plug, an accident may occur and thus the existing ozone supply system is not safe.

In addition, the existing home system ignores personal safety protection. It does not have a safety device to prevent child from falling. When a child reaches a hazardous area, such as a balcony, window, or mezzanine corridor, the child may fall if there is no alarm device.

Also, the existing smart home system does not have alarm and rescue functions for elderly or disabled when they fall in places such as the bathroom or the kitchen and cannot stand up by themselves. Because there is no alarm system in existing smart home systems, the elderly and disabled may not receive quick assistance and rescue.

Furthermore, the existing home system does not have a prevention system for water overflow when the user forgets to turn off the water or the water pipes are broken. Water overflow often causes damages to furniture and electrical appliances, thus causing great losses to home owners. The existing home system does not have water leak prevention device, therefore furniture, electrical appliances and other properties cannot be adequately protected.

Technical Solutions

The main objective of the invention is to provide a smart home system which has a safer, more convenient, and multichannel ozone supply system.

The second objective of the invention is to provide a smart home system which prevents children from unexpected falling.

The third objective of the invention is to provide a smart home system which can detect and send an alarm when a human falls.

The fourth objective of the invention is to provide a smart home system which has a water leak prevention system.

A fifth objective of the invention is to provide an operation method for the smart home system.

To achieve the first objective, the invention provides a smart home system which comprises an ozone supply system. The ozone supply system comprises a controller which controls the ozone generator, at least two gas supply outlets, each of which is connected with a gas outlet of the ozone generator through a pipe, and first solenoid valves which control opening or closing of the gas supply outlets. The controller is electrically connected with each of the first solenoid valves and controls the opening and the closing of the solenoid valves.

A preferred scheme is that the ozone supply system comprises at least one water terminal, each of the water terminals is connected to a water outlet of a gas-liquid mixer, the water inlet of the gas-liquid mixer is connected to a water inlet pipe, a water flow sensor is installed inside each of the water inlet pipes, and the sensors send signals to the controller.

A further preferred scheme is that the controller has a memory which stores the ozone flow rate thresholds for the gas supply outlets, and the gas supply outlets are provided with gas flow rate sensors. The gas flow rate sensors detect the ozone gas flow rate and send the results to the controller.

An even further preferred scheme is that the smart home system further comprises a water leak prevention system. The water leak prevention system comprises a water flow rate sensor which detects the water flow inside the water inlet pipe and sends the data to the controller and a motion sensor which detects human body signal and sends the signal to the controller. The controller comprises a memory which stores the duration thresholds for which the human body does not move and the second solenoid valves which control opening and closing of the house water inlet pipe. The controller is electrically connected with the second solenoid valves and controls opening and closing of the second solenoid valves.

A still further preferred scheme is that the smart home system comprises a falling alarm system and a motion sensor to detect human body motion and sends the signal to the controller. The controller has a memory which stores the duration thresholds for which the human body does not move. The alarm system receives the signal from the controller and issues alarms accordingly.

Another preferred scheme is that the smart home system comprises a child falling prevention system. The child falling prevention system comprises a signal generator which is carried by the child and a signal receiver which is placed in hazardous areas. The signal receiver receives signals from the signal generator and sends them to the controller. The child falling prevention system further comprises an alarm device which receives signals from the controller and issues alarms accordingly. The controller also comprises a memory which stores the duration thresholds.

To achieve the fifth objective, the invention provides an operation method for the above smart home system. The method comprises the controller driving the ozone generator to generate ozone and transport it to the gas-liquid mixer through a pipe; the central processor determining whether it receive a signal to open the first solenoid valve and if so, providing an opening signal to the first solenoid valve; the gas flow rate sensor detecting the ozone flow rate passing through the gas inlet of the gas-liquid mixer and sending the data to the controller; the controller determining whether the ozone flow rate passing through the gas inlet is greater than the ozone flow rate threshold, and if so, providing a signal to the first solenoid valve in the gas inlet to reduce the opening level of the first solenoid valve.

Effectiveness of the Invention

The smart home system of the invention utilizes a central ozone supply system which eliminates the need for multiple ozone generators. According to the invention, ozone is supplied from the central ozone supply system to multiple gas supply outlets. The invention makes the ozone use for home disinfection safer and more convenient and it improves people's quality of life. The invention also achieves multiple-channel ozone gas supply.

In addition, ozone from the ozone generator is sent through the pipeline to gas-liquid mixers wherein ozone is mixed with tap water to form ozone water and the ozone water is then supplied to each water terminal. Therefore, there is no need for each faucet to have one ozone generator and thus there is no need to have electrical plugs nearby the faucets. The invention reduces accidents which may be caused by water splashing onto electrical plugs.

Further, the smart home system detects, by the gas flow sensor, the amount of ozone flowing through the gas-liquid mixer. This helps control the usage of ozone at each water terminal and avoids over usage of ozone.

Also, if the motion sensor cannot detect human signals for a time period which is greater than the duration threshold value the controller recognizes no one is home. If the water flow sensor can detect water flowing through the water inlet pipe within this time period, it indicates that the water pipe is broken or the user forgot to turn off the faucet. The controller will then turn off the water via the second solenoid valve to avoid water overflow and damage to the home property.

Further, the motion sensor detects human motion signals and sends the signals to the controller, and the controller detects human motion in the bathroom, kitchen, stairs, and bedrooms. If human motion cannot be detected for a long time, it considers whether someone has fallen in a specified place, and the alarm will go on to alert family members or neighbors to come quickly to rescue.

In addition, when a child stays close to a dangerous place such as balcony, window or mezzanine corridor for a long period of time, the controller considers whether that the child is in a dangerous zone, and the alarm will go on to alert adults in the house to quickly come and lead the child away from the dangerous zone to avoid the child from falling.

Figure 1:
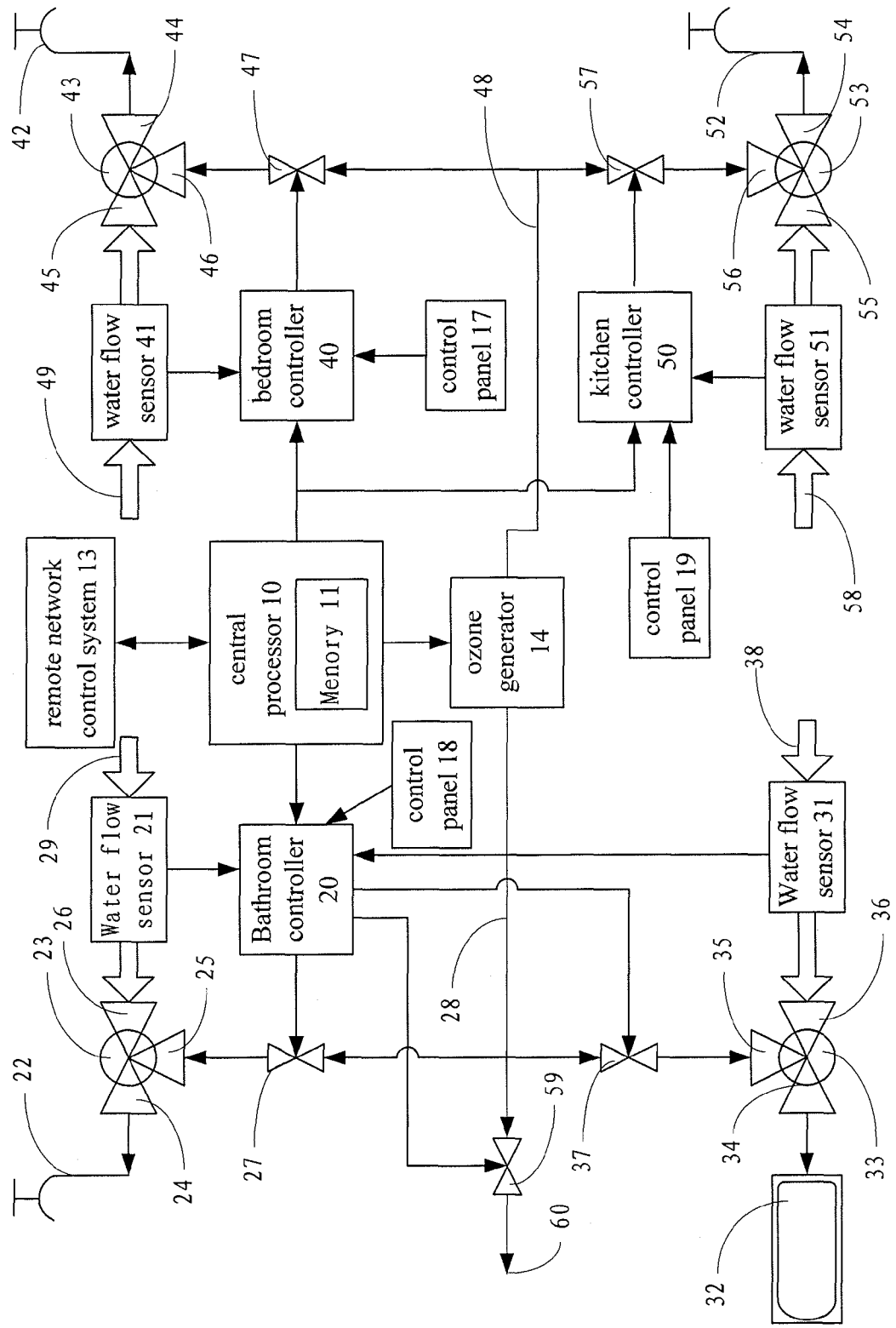
FIG. 1 is a schematic block diagram of the ozone supply system of an embodiment of the smart home system of the invention.

The invention is further illustrated by the combination of the drawings and the embodiments as follows.

EMBODIMENTS

The smart home system of the invention comprises an ozone supply system, a water leak prevention system, a falling alarm system, and a child falling prevention system. These systems are described individually as follows, Ozone Supply System See FIG. 1. The ozone supply system of this embodiment comprises a controller. The controller comprises a central processor 10, bathroom controller 20, bedroom controller 40, and kitchen controller 50. These controllers are controlled by the central processor 10. The central processor 10 is provided with the memory 11. The memory 11 stores the ozone flow rate thresholds. Each of the ozone flow rate threshold corresponds to a water terminal. Of course, the central processor 10 may send the stored ozone flow rate thresholds to the bathroom controller 20, the bedroom controller 40, and the kitchen controller 50. Further, the central processor 10 communicates with the remote network control system 13, receives external signals, and sends signals about the home system to outside.

The ozone supply system comprises an ozone generator (14) which is connected with and is controlled and driven by the central processor (10) to generate ozone gas.

The bathroom controller 20 controls the ozone supply for more than one water terminals. In this embodiment, the water terminals can be faucets, bathrooms, bathtubs, washbasins, and water heaters etc. In FIG. 1, the faucet 22 as a water terminal is connected to the water outlet 24 of the gas-liquid mixer 23. The water inlet 26 of the gas-liquid mixer 23 is connected with the water inlet pipe 29. The water flow sensor 21 is installed inside the water inlet pipe 29 and is used to detect the water flow inside the water inlet pipe 29.

The gas inlet 25 of the gas-liquid mixer 23 is connected to the pipe 28. The ozone gas, which is generated by the ozone generator 14, is transported to the pipe 28. Therefore, the pipe 28 is filled with ozone gas. The solenoid valve 27 is installed inside the gas inlet 25 of the gas-liquid mixer 24. The solenoid valve 27 is connected to the bathroom controller 20. Opening and closing of the solenoid valve 27 is controlled by the bathroom controller 20. The connection point of the pipe 28 with the gas inlet 25 is the ozone gas supply outlet.

The gas flow rate sensor is installed inside the gas inlet 25 of the gas-liquid mixer 24 and it detects the ozone gas flow rate passing through the gas inlet 25 and sends the data to the bathroom controller 20.

The central processor 10 drives the ozone generator 14 when the smart home system is working. The ozone generator 14 generates ozone and the ozone is transported to the pipe 28. The solenoid valve 27 is closed when tap water in the pipe 29 is not flowing. When the user turns on the faucet 22, the water flow sensor 21 detects the water flow signal and sends it to the bathroom controller 20; the bathroom controller 20 gives an opening signal to the solenoid valve 27 and the solenoid valve 27 then opens. The ozone gas enters into the gas inlet 25 of the gas-liquid mixer 23, and is mixed in the gas-liquid mixer 23 with tap water to form ozone water which flows out through the faucet 22. When the water flow sensor 21 does not detect the flow signal, the bathroom controller 24 gives a closing signal to the solenoid valve 27, and the ozone gas will not flow into the gas-liquid mixer 23.

The water terminal in the bathroom comprises the tub 32. The water outlet of the tub 32 is connected to the water outlet 34 of the gas-liquid mixer 33. The water inlet 36 of the gas-liquid mixer 33 is connected to the inlet pipe 38. The gas inlet 35 of the gas-liquid mixer 33 is connected to the pipe 28 and the gas inlet 35 is provided with a solenoid valve 37, which is controlled by the bathroom controller 20 to open and close.

The water inlet 38 is provided with the water flow sensor 31 which is used to detect the water flow signal of the inlet pipe 38 and to send the signal to the controller 20. The bathroom controller 20 controls opening or closing of the solenoid valve 37 according to the received signal.

Of course, the ozone gas does not necessarily need to be mixed with tap water to form ozone water. The ozone gas can be directly transported through a separate pipe and can be used for goods disinfection or entire bathroom disinfection. It can also be directly emitted in a certain amount to wardrobes or shoeboxes to disinfect clothing or shoes. As shown in FIG. 1, one end of the pipe 28 is provided with a separate gas outlet 60. At the gas outlet 60 is installed the solenoid valve 59 which is connected to the bathroom controller 20. Opening and closing of the solenoid valve 59 is controlled by the bathroom controller 20. In addition, the bathroom controller 20 is also connected to a control panel 18 which is used as an input device in this embodiment. Through the control panel 18, one can input a control signal to the bathroom controller 20 to control the solenoid valve 59. The bathroom controller controls the solenoid valve 59 according to the signals received.

The central processor 10 controls the bedroom controller 40 and the bedroom controller 40 controls opening and closing of the solenoid valve 47 inside the gas inlet 46 of the gas-liquid mixer 43. The water outlet 44 of the gas-liquid mixer 43 is connected to the faucet 42 at the water terminal. The water inlet 45 of the gas-liquid mixer 43 is connected to the inlet pipe 49. Inside the inlet pipe 49 is equipped with a water flow sensor 411. The gas inlet 46 of the gas-liquid mixer 43 is connected with one end of the pipe 48. The other end of the pipe 48 is connected to the ozone generator 14. Therefore, the pipe 48 is filled with ozone gas. The bedroom controller 40 is also connected to the control panel 17. The user can use the control panel 17 to input the control signal to the solenoid valve 47 to control the opening and closing of the solenoid valve 47.

The central processor 10 also controls the kitchen controller 50 and the kitchen controller 50 controls the opening and the closing of the solenoid valve 57 which is located on the gas inlet 56 of the gas-liquid mixer 53. The gas inlet 56 of the gas-liquid mixer 53 is connected to the pipe 48. The water inlet 55 is connected with the water inlet pipe 58. The inside of the water inlet pipe 58 is equipped with a water flow sensor 51 which is used to detect the water flow inside the pipe 58 and send the signals to the kitchen controller 50. The water outlet 54 of the gas-liquid mixer 53 is connected to the water faucet 52 as the water terminal. The kitchen controller 50 is also connected with the control panel 19. The user can use the control panel 19 to input the control signals to the solenoid valve 57 and control opening and closing the solenoid valve 57.

The gas flow rate sensors are placed inside the gas inlets 35, 46, and 56 the gas-liquid mixers 33, 43, and 53. The gas flow rate sensors are used to detect the ozone flow rates passing through the gas inlets 35, 46, and 56 and send the data to the bathroom controller 20, the bedroom controller 40, and the kitchen controller 50.

When the ozone supply system is working, the users can use the control panels 17, 18, and 19 to control the opening and closing of each of the solenoid valves and control the amount of ozone supply for each gas supply outlet. Thus, the user may control the time for the opening and closing of specific solenoid valves according to the actual need of the ozone amount. The ozone supply is not directly dependent on the water flow; and thus the ozone supply is more flexible.

In addition, suitable faucets for this embodiment can be those disclosed in Utility Model Patent Application Publication No. CN2016280151U. The faucet comprises a main faucet body and a casing. The inside of the casing is equipped with a contractible hose. The contractible hose is much longer than the main body or the casing, and therefore the user can pull out the contractible hose. There is a three-way tube under the main body. One end of the three-way tube is connected with the water inlet pipe, and the other end of the three-way tube is connected through a pipe to the ozone generator. The tube is equipped with a check valve. The third end of the three-way tube is connected to the contractible hose. Because the main body is equipped with a water flow regulating valve, the tap water and the ozone gas can, respectively, pass through the contractible hose.

Therefore, when the user needs tap water, he can turn off the solenoid valve of the ozone supply pipe and open the water valve to use tap water. If the user only needs to use the ozone gas, he can turn off the water flow valve and open the solenoid valve and get the ozone gas by pulling out the contractible hose. If the user needs ozone water, he can open the water flow valve and the solenoid valve at the same time. Of course, the user can also use the washbasin and the other containers to hold tap water, pull out the contractible hose and put the hose outlet into the tap water, open the solenoid valve to release the ozone gas, and the ozone gas is then dissolved in the tap water to form ozone water.

Of course, in the ozone supply system of this embodiment, the water flow sensor does not have to be installed inside the water inlet pipe. The water flow sensor can be installed on an input device. The input device is connected to the central processor. Opening and closing of each of the solenoid valves can be set through the input device to control the ozone gas supply.

Further, the solenoid valves of this embodiment are adjustable solenoid valves. The users can input signals from the control panels 17, 18, and 19 to adjust the power level for each of the solenoid valves and control the ozone gas flow for each of the gas supply outlets. In addition, the user can also set up opening and closing times for each of the solenoid valves to conveniently use ozone gas.

Figure 2:
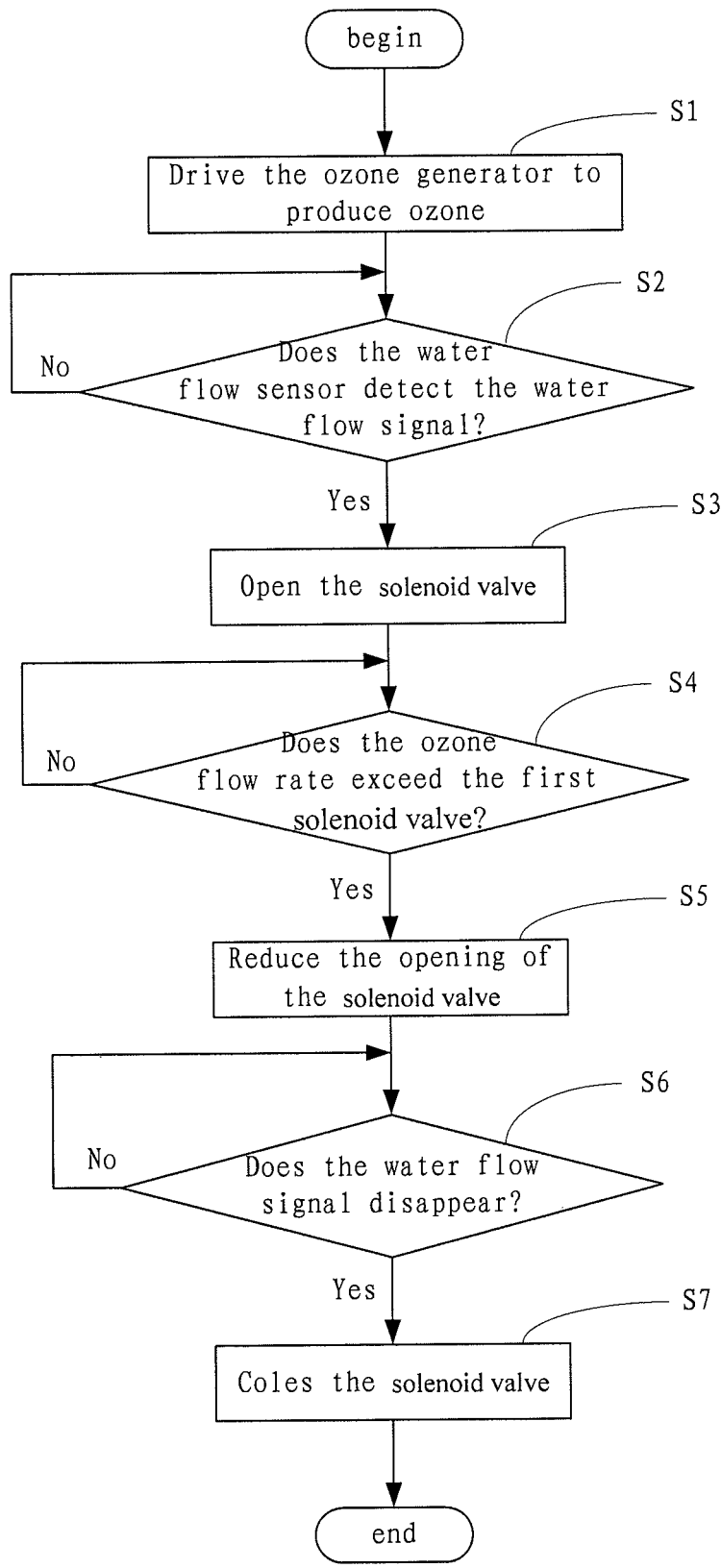
FIG. 2 is a flow diagram of the operation method of the invention for the smart home system.

Also, this embodiment can use the signal from the water flow sensor as a signal to close the solenoid valve. See FIG. 2. When the ozone supply system is working, the central processor performs step S1 to drive the ozone generator to work, and the ozone generator generates the ozone gas and transports it to the pipe. The controllers, such as the bathroom controller, the kitchen controller and the bedroom controller etc., determine whether the water flow sensors can detect the water signals, i.e., perform step S2. If water flow signal is detected, the central processor then performs step S3 and it turns on the corresponding solenoid valve of the water inlet pipe where the water flow sensor is installed. The ozone gas inside the pipe flows through the solenoid valve into the gas-liquid mixer to form ozone water.

In this embodiment, the signal from the water flow sensor to the bathroom controller is used as a signal to open the solenoid valve. Alternatively, the user can input the control signal to the solenoid vale via the control panel. For instance, the user may input a signal for opening the solenoid valve 27 and the bathroom controller will send the opening signal to the solenoid valve 27 to control the solenoid valve.

When the solenoid valve is open, the gas flow controller of the gas-liquid mixer detects the ozone gas flow rate passing through the gas inlet of the gas-liquid mixer, and the bathroom controller, the kitchen controller, and the bedroom controller will perform step S4 and determine whether the ozone gas flow rate passing through the gas inlet is greater than the corresponding threshold for the water terminal. If the ozone gas flow rate is not greater than the threshold, controllers will continue detecting; if the ozone gas flow rate is greater than the threshold, the controllers will perform step S5 and issue a signal to reduce the degree of the opening of the solenoid valves and reduce the ozone gas flow rate through the gas inlet.

Finally, the bathroom controller, the kitchen controller and the bedroom controller determine whether the water flow signal of the water flow sensor disappears, i.e., perform step S6. If the signal disappears, it indicates that the faucets and other water terminals are closed. The controller will send closing signals to the corresponding solenoid valves stopping the ozone gas supply to the gas-liquid mixer.

According to the above scheme, the smart home system is provided with only one ozone generator and the ozone generator supplies ozone gas to multiple water terminals. This smart home system greatly improves the convenience for home ozone use. Further, the smart home system does not require the power plugs to be installed near the faucets or water terminals. It can thus avoid accidents which may occur when water splashes onto the power plugs.

The Water Leak Prevention System

Figure 3:
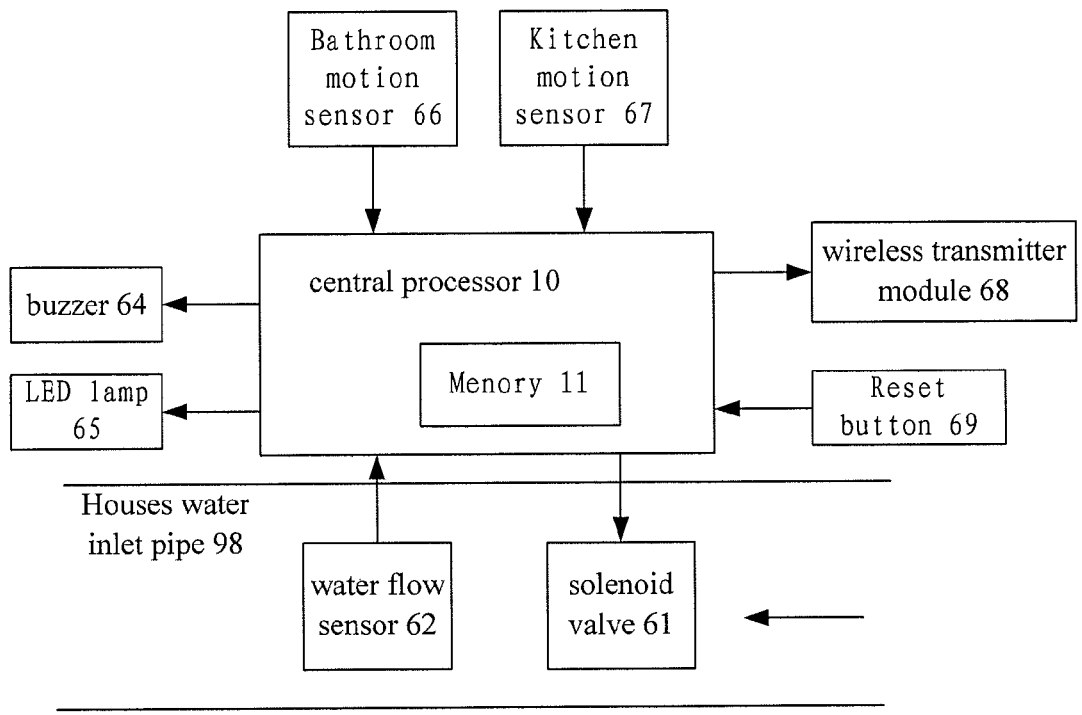
FIG. 3 is a schematic block diagram of the embodiment of the water leak prevention system of the smart home system of the invention.

See FIG. 3. The smart home system further comprises motion sensors which are connected with the central processor 10, including the bathroom motion sensor 66 and the kitchen motion sensor 67. Of course, more motion sensors can be installed.

The motion sensors are used to detect human body signals and human motion signals through infrared detectors and microwave detectors. Within the detection range of the motion sensor, the motion sensor can detect the human motion signal and send the signal to the central processor 10. If human body does not move for a long time, the motion sensor will consider there is a human body but that the human does not move. If within the detection range of the motion sensor there is no human body, the motion sensor will not detect human signals, such as the body temperature, etc.

The water leak prevention system comprises the solenoid valve 61 which is installed inside the house water inlet pipe 98 and the water flow sensor 62. The solenoid valve 61 is at the upstream of the water flow sensor 62. In the house water inlet pipe 98, the water flow direction is shown in FIG. 3.

The central processor 10 is connected to the alarm device. The alarm device comprises the buzzer 64, the LED lamp 65 as a light-emitting device, and the radio transmitter module 68 as a remote alarm device. The central processor 10 determines whether water leaks in the house and gives the alarm signal via the alarm device.

In addition, the central processor is also connected with the input device and the input device comprises the solenoid valve reset button 69. When there is a large amount of water stored for a long time while there is no human motion in the bathroom or the kitchen, the central processor 10 may misjudge whether a person is in the bathroom or kitchen while the tap water is running, and the solenoid valve 61 will be mistakenly closed. Therefore, it is necessary to have a manual reset button 69 so that the solenoid valve 61 can be reset.

The memory 11 of the central processor 10 stores a duration threshold for the absence of human signal. If the time during which no human signal can be detected is greater than the duration threshold, the central processor will determine there is no one in the bathroom or the kitchen.

When the water leak prevention system is working, the water flow sensor 62 detects the water flow in the house water inlet pipe 98. If the water flow sensor detects water flow, water is possibly leaking. At the same time, the bathroom motion sensor 66 and the kitchen motion sensor 67 detect the human activity signal and transmit the signal to the central processor 10. If the central processor 10 finds that the bathroom motion sensor 66 and the kitchen motion sensor 67 do not detect human signals, it will determine whether the time period during which the motion sensors do not detect human signals is longer than the duration threshold; if it is longer, that means water is leaking, and the central processor 10 will then send a closing signal to the solenoid valve 61, the solenoid valve 61 will be closed so that water leakage can be avoided.

Of course, when the central processor 10 detects human motion signals within the duration threshold, it terminates the detection cycle; and it restarts a new detection cycle when the human motion signal disappears. When the water flow sensor 62 can no longer detect the water flow signal, the bathroom motion sensor 66 and the kitchen motion sensor 67 will stop working.

After the central processor 10 determines there is water leakage, it gives sound or light alarm signals via the buzzer 64 and LED lamp 65; alternatively, it transmits the alarm signal by the wireless transmitter module 68, dialing a specific phone number or sending a specific text message to a cell phone.

Of course, the water flow rate sensor can also be installed in the water inlet pipes which are connected to each of the water terminals, and thus it can more precisely tell which water terminal has not been turn off or which pipeline is broken.

Falling Alarm System

Figure 4:
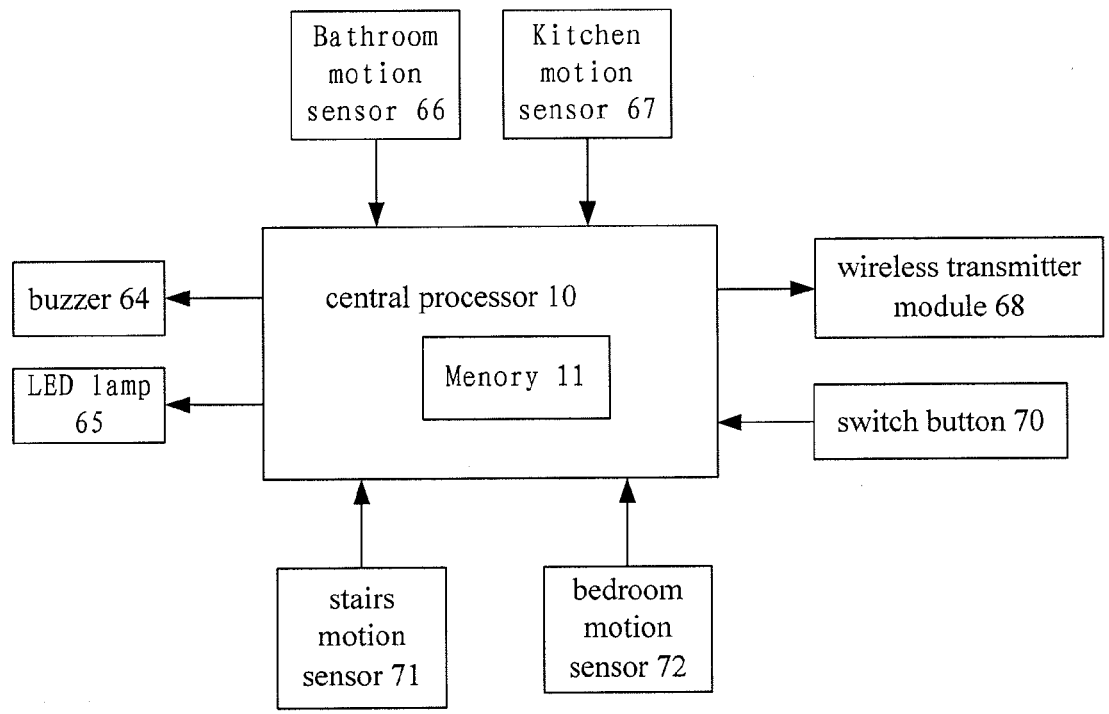
FIG. 4 is a schematic block diagram of the embodiment of the falling alarm system of the smart home system of the invention.

See FIG. 4. The falling alarm system of this embodiment comprises the bathroom motion sensor 66, the kitchen motion sensor 67, the stairs motion sensor 71, and the bedroom motion sensor 72. These sensors are connected with the central processor 10 and they detect human motion signals. The falling alarm system further comprises the buzzer 64, the LED lamp 65, and the wireless transmitter module 68 which is connected to the central processor 10. The memory 11 of the central processor 10 stores a duration threshold for how long there can be no human motion to determine when human falling occurs.

After the falling alarm system starts, the bathroom motion sensor 66, the kitchen motion sensor 67, the stairs motion sensor 71, the bedroom motion sensor 72 and other motion sensors perform real-time detection of human motion and sends the detected signal to the central processor 10. After the central processor 10 receives the transmitted signal by the motion sensors, it decides whether there is a human body remaining stationary for a long time, and if so, it determines whether the stationary time is longer than the threshold value; and if so, it considers whether the person might have fallen and issues an alarm signal, or calls a specific phone number or sends a specific text message to a cell phone through the wireless transmitter module 68.

When the central processor 10 determines someone has fallen, it can also send closing signals to the solenoid valves which are installed inside the house water inlet pipe to turn off the faucets and other water terminals to avoid the fallen person drowning.

Of course, when people take a long bath or sleep at night, there will be a long time of no human body motion in the bathroom or bedroom. Therefore, the falling alarm system is provided with a switch button 70 which is connected to the central processor 10. The user can press the switch button 70 to turn off the falling alarm system and avoid a false alarm.

Child Falling Prevention System

Figure 5:
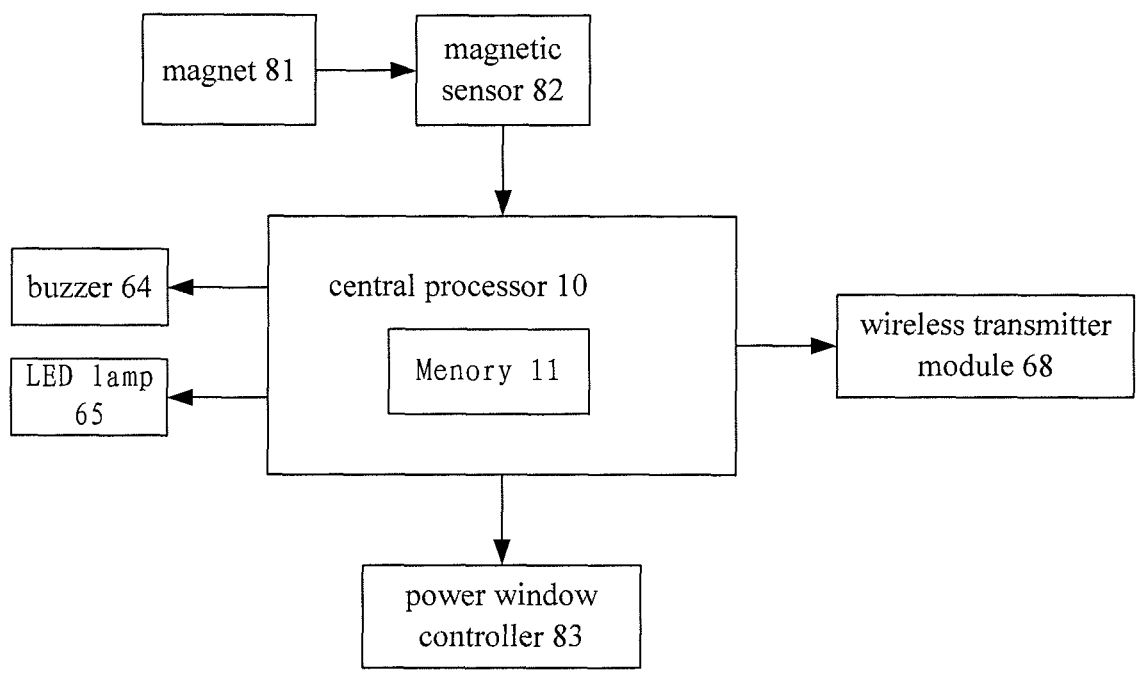
FIG. 5 is a schematic block diagram of the embodiment of the child falling prevention system of the smart home system of the invention.

See FIG. 5. The child falling prevention system comprises a signal generator placed with the child, for example, in this embodiment, the magnet 81 or other magnetic materials, and a signal receiver is placed on balconies, windows, and mezzanine corridors or other danger zones, for example, the magnetic sensor 82. The magnetic sensor 82 sends via a wired or wireless manner the received signal to the central processor 10.

The memory 11 of the central processor 10 stores a duration threshold value. This duration threshold value is a threshold value for the time period during which the signal receiver receives the signal from the signal generator. When the time period during which the magnetic sensor 82 receives a magnetic signal from the magnet 81 is longer than the duration threshold, it means that the child is in the hazardous area and has possibility fallen. Therefore, the central processor 10 will send an alarm signal for relief measures.

In this embodiment, the central processor 10 is connected with the buzzer 64, the LED lamp 65 and other sound and light alarm devices, and it is also connected with the remote wireless transmitter module 68. When the central processor 10 receives signals from the magnetic sensor 82 and other signal receivers, it judges whether the duration of the signals is longer than the threshold value. If the duration of the signal is longer than the threshold value, it will issue an alarm signal, or dials a specified phone number or sends a text message to a cell phone through the wireless transmitter module 68.

In addition, the present embodiment also comprises a power window controller 83 which is connected with the central processor 10. The power window controller is installed on a power window which can automatically close the window. Suitable power windows include those disclosed in Chinese Utility Model Patent Application Publication No. CN201605943U. When the central processor 10 determines the child is at risk of falling, it will send a signal to the power window controller 83 to automatically close the power window to prevent the child from falling out the window.

Of course, suitable signal generators are not limited to magnets. They can also be radio signal generators. The corresponding signal receivers can then be radio signal receivers.

In addition to the ozone supply system, the water leak prevention system, the falling alarm system, and the child falling prevention system, the smart home system of the invention can also comprise the carbon monoxide detection and alarm system and the negative ion supply system. The carbon monoxide detection and alarm system comprises one or more carbon monoxide detectors located in the kitchen and bathroom for detecting the carbon monoxide concentrations. If the carbon monoxide concentration exceeds the standard value, the central processor will issue an alarm. The negative ion supply system comprises a negative ion generator which provides negative ion to the air outlets for fresh air.

Of course, the above-described embodiments are only preferred examples of the invention. Many changes to these embodiments can be made. For instance, several water terminals can share one gas-liquid mixer to generate ozone water; or the gas inlets of the gas-liquid mixer are not provided with the gas flow rate sensors, and each of the solenoid valves installed at the gas inlets can be preset with a degree of opening. These changes can still achieve the objectives of the invention.

Finally, it should be emphasized that the invention is not limited to the above embodiments. For example, alternation to the flow rate threshold values, alternation to the duration threshold values for human body to not move, and many other changes will still fall within the scope of the claimed invention.

INDUSTRIAL APPLICABILITY

According to the smart home system of the invention, a central ozone supply can be achieved. During home renovation, there is no need for installing multiple ozone generators. Ozone from the ozone generator can be delivered to multiple gas outlets through pipelines. The invention greatly improves the convenience and safety for using ozone for home disinfection and for health care. Thus the invention improves the quality of people's life. In addition, the smart home system may have only one ozone generator which provides ozone gas to multiple gas outlets, and each of the gas outlets controls the ozone supply through the solenoid valves to achieve the flexibility of the ozone use at each of the gas outlet. The invention provides people with a healthy and comfortable home environment.

What is claimed is:

1. A smart home system, comprising:
an ozone supply system, comprising
a controller which controls an ozone generator;
two or more gas supply outlets which are connected with the gas outlets of the ozone generator through pipes; and
first solenoid valves which control opening and closing of the gas supply outlets; wherein the controller is electrically connected with each of the first solenoid valves and controls opening and closing of each the first solenoid valves;
wherein the ozone supply system further comprises one or more water terminals; wherein each of the water terminals is connected to a water outlet of a gas-liquid mixer; wherein each of gas inlets of each gas-liquid mixer is connected to the gas supply outlet; and each of the water inlet of the gas-liquid mixer is connected with the water inlet pipe; and wherein a water flow sensor is installed inside the water inlet pipe which transmits the detected signals to the controller.

2. The smart home system of claim 1, wherein each of the water outlets of each of the gas-liquid mixers is connected to one or more water terminals.

3. The smart home system of claim 2, wherein the controller comprises a memory and stores the ozone flow rate thresholds for all of the gas supply outlets; and wherein the gas supply outlets are provided with gas flow sensors which detect the ozone gas flow rates and transmit the detected data to the controller.

4. The smart home system of claim 3, wherein there are multiple flow rate thresholds and each of said flow rate thresholds corresponds to a corresponding gas supply outlet.

5. The smart home system of claim 2, which comprises a water leak prevention system which comprises:
water flow rate sensors installed inside the water inlet pipes, wherein each of the water flow rate sensors detects the water flow rate in the water pipes and transmits the detected data to the controller;

motion sensors which detect human signal and transmit the detected signal to the controller; wherein the controller has a memory for storing a duration threshold for human signal; and second solenoid valves which control opening and closing of a house water inlet pipe, wherein the controller is electrically connected with the second solenoid valves and controls opening and closing of the second solenoid valve.

6. The smart home system of claim 2, further comprising a falling alarm system, wherein the falling alarm system comprises:
a motion sensor which detects human motion signals and transmit the detected signals to the controller; wherein the controller has a memory which stores duration threshold for which human body does not move; and
an alarm device which receives the signals transmitted from the controller and issues alarm signals accordingly.

7. The smart home system of claim 2, further comprising a child falling prevention system which comprises:
a signal generator placed with the child;
a signal receiver placed in a hazardous area which receives the signals from the signal generator and transmits the signals to the controller;
an alarm device which receives the signals from the controller and issues an alarm signal accordingly;
wherein the controller further comprises a memory which stores a duration threshold.

8. The smart home system of claim 1, wherein there are multiple flow rate thresholds and each of said flow rate thresholds corresponds to a corresponding gas supply outlet.

9. A smart home system, comprising:
an ozone supply system, comprising
a controller which controls an ozone generator;
two or more gas supply outlets which are connected with the gas outlets of the ozone generator through pipes; and
first solenoid valves which control opening and closing of the gas supply outlets; wherein the controller is electrically connected with each of the first solenoid valves and controls opening and closing of each the first solenoid valves,
wherein the controller comprises a memory and stores the ozone flow rate thresholds for all of the gas supply outlets; and wherein the gas supply outlets are provided with gas flow sensors which detect the ozone gas flow rates and transmit the detected data to the controller.

10. The smart home system of claim 9, wherein there are multiple flow rate thresholds and each of said flow rate thresholds corresponds to a corresponding gas supply outlet.

11. A smart home system, comprising:
an ozone supply system, comprising
a controller which controls an ozone generator;
two or more gas supply outlets which are connected with the gas outlets of the ozone generator through pipes; and
first solenoid valves which control opening and closing of the gas supply outlets; wherein the controller is electrically connected with each of the first solenoid valves and controls opening and closing of each the first solenoid valves;
the smart home system further comprising a water leak prevention system which comprises:
water flow rate sensors installed inside the water inlet pipes, wherein each of the water flow rate sensors detects the water flow rate in the water pipes and transmits the detected data to the controller;

motion sensors which detect human signal and transmit the detected signal to the controller; wherein the controller has a memory for storing a duration threshold for human signal; and
second solenoid valves which control opening and closing of a house water inlet pipe, wherein the controller is electrically connected with the second solenoid valves and controls opening and closing of the second solenoid valve.

12. A smart home system, comprising:
an ozone supply system, comprising
a controller which controls an ozone generator;
two or more gas supply outlets which are connected with the gas outlets of the ozone generator through pipes; and
first solenoid valves which control opening and closing of the gas supply outlets; wherein the controller is electrically connected with each of the first solenoid valves and controls opening and closing of each the first solenoid valves,
wherein the smart home system further comprises a falling alarm system, wherein the falling alarm system comprises:
a motion sensor which detects human motion signals and transmit the detected signals to the controller; wherein the controller has a memory which stores duration threshold for which human body does not move; and
an alarm device which receives the signals transmitted from the controller and issues alarm signals accordingly.

13. A smart home system, comprising:
an ozone supply system, comprising
a controller which controls an ozone generator;
two or more gas supply outlets which are connected with the gas outlets of the ozone generator through pipes; and
first solenoid valves which control opening and closing of the gas supply outlets; wherein the controller is electrically connected with each of the first solenoid valves and controls opening and closing of each the first solenoid valves;
the smart home system further comprising a child falling prevention system which comprises:
a signal generator placed with the child;
a signal receiver placed in a hazardous area which receives the signals from the signal generator and transmits the signals to the controller;
an alarm device which receives the signals from the controller and issues an alarm signal accordingly;
wherein the controller further comprises a memory which stores a duration threshold.

14. A method for operating a smart home system, wherein the smart home system comprises:
a controller which is used to control an ozone generator;
two or more gas supply outlets, wherein each of the gas supply outlets is connected through a pipe with a gas outlet of the ozone generator; and the gas outlet is provided with a gas flow sensor which detects the ozone gas flow and transmits the detected data to the controller;
first solenoid valves which control opening and closing of the gas supply outlets, wherein the controller is electrically connected with each of the first solenoid valves and controls opening and closing of each of the first solenoid valves;
water terminals, wherein each of the water terminals is connected to a water outlet of a gas-liquid mixer and each of the water outlet of each of the gas-liquid mixers is connected to two or more water terminals; each of the gas supply inlets of the gas-liquid mixer is connected to the gas supply outlet; and each of the water inlets of the gas-liquid mixer is connected with the water inlet pipe;

wherein the controller comprises a memory which stores the ozone flow rate thresholds of the gas supply outlets;

the method comprising:

the controller driving the ozone generator to generate ozone and transport ozone through to the gas-liquid mixer via pipe;

the controller determining whether it receives an external signal to open the first solenoid valve and if so, it provides a opening signal to the first solenoid valve;

the gas flow rate sensor detecting the ozone flow rate passing through the gas inlet of the gas-liquid mixer, and transmitting the detected data to the controller; the controller determining whether the ozone flow rate is greater than the ozone flow rate threshold, and if so, providing a signal to the first solenoid valve located in the gas inlet to reduce the opening level of the first solenoid valve; and the controller determining whether it receives an external signal to close the first solenoid valve, and if so, providing to the first solenoid valve a closing signal.

15. The method of claim 14, wherein there are multiple flow rate thresholds and each of the flow rate thresholds corresponds to a gas supply outlet; and wherein after the controller receives the data from the gas flow rate sensor, it determines whether the data is greater than the corresponding flow rate threshold for the gas supply outlet where the gas flow sensor is installed.

* * * * *